United States Patent [19]

Ogawa et al.

[11] Patent Number: 4,609,426

[45] Date of Patent: Sep. 2, 1986

[54] METHOD AND APPARATUS FOR MONITORING ETCHING

[75] Inventors: Yoshifumi Ogawa; Masaharu Nishiumi; Yoshie Tanaka, all of Kudamatsu; Sadayuki Okudaira, Oume; Shigeru Nishimatsu, Kokubunji, all of Japan

[73] Assignee: Hitachi, Ltd., Tokyo, Japan

[21] Appl. No.: 736,769

[22] Filed: May 22, 1985

[30] Foreign Application Priority Data

May 23, 1984 [JP] Japan .............................. 59-102523

[51] Int. Cl.$^4$ ..................... H01L 21/306; B44C 1/22; C03C 15/00; C23F 1/02
[52] U.S. Cl. .................... 156/626; 156/627; 156/643; 156/646; 156/345; 204/298; 204/192.33
[58] Field of Search ............... 156/626, 627, 643, 646, 156/653, 659.1, 657, 662, 345, 656; 204/192 E, 298; 356/72, 313, 316, 437

[56] References Cited

U.S. PATENT DOCUMENTS

| | | | |
|---|---|---|---|
| 4,263,088 | 4/1981 | Gorin | 156/626 |
| 4,345,968 | 8/1982 | Coe | 156/627 |
| 4,356,055 | 10/1982 | Montier | 156/626 |
| 4,415,402 | 11/1983 | Gelernt et al. | 156/626 |

FOREIGN PATENT DOCUMENTS

| | | | |
|---|---|---|---|
| 57-26438 | 2/1982 | Japan | 156/626 |
| 0140127 | 8/1983 | Japan | 156/626 |

*Primary Examiner*—William A. Powell
*Attorney, Agent, or Firm*—Antonelli, Terry & Wands

[57] ABSTRACT

This invention relates to a method and apparatus for monitoring etching. The monitor method comprises the steps of regulating a gas pressure inside a treating chamber, in which a sample is being etched by a dry etching process, to a pressure at which a emission line spectrum can be clarified, converting the gas whose pressure is regulated to plasma, and monitoring the etching state of the sample from the change of the intensity of the emission line spectrum with time. The monitor apparatus comprises exhaust means for discharging a gas from a treating chamber in which a sample is being etched by a dry etching process, plasma means for introducing the gas discharged from the treating chamber and converting it plasma, pressure regulation means for regulating the pressure of the gas at the plasma means to a pressure at which a emission line spectrum can be clarified, and spectrum detection means for detecting the emission line spectrum of the plasma at the plasma means, and detecting the change of the intensity of the detected emission line spectrum with time.

11 Claims, 6 Drawing Figures

4,609,426

METHOD AND APPARATUS FOR MONITORING ETCHING

BACKGROUND OF THE INVENTION

1. Field of the Invention

This invention relates generally to a method and apparatus for monitoring etching, and more particularly to a method and apparatus for monitoring etching which is suitable for monitoring the state of progress of etching of a sample to be etched by a dry etching process.

2. Description of the Prior Art

An etching apparatus for treating a sample by a dry etching process such as a plasma etching process is disclosed, for example, in Japanese Patent Laid-Open No. 84431/1983. In this apparatus, a discharge portion for detecting the intensity of an emission spectrum is disposed afresh on the downstream side of the flow of a reactive gas with respect to an etching portion where the sample is to be etched by plasma.

The apparatus described above controls the discharge of the discharge portion independently of the etching portion, and introduces the gas generated by etching in the etching portion into the discharge portion and discharges the gas so that an inherent emission is generated efficiently and the decrease of the concentration of an active group due to etching is susceptibly responsive to the change of intensity of the emission spectrum.

However, this apparatus does not particularly consider how to control the gas pressure of the discharge portion. In other words, since the discharge portion is disposed at an exhaust pipe portion where the gas pressure is not at all controlled, the bright line spectrum at the discharge portion will become ambiguous if the emission line spectrum occurring at the etching portion is ambiguous, particularly when the same method of applying an electromagnetic field is employed for both the etching portion and the discharge portion. Therefore, the state of etching of the sample at the etching portion can not be monitored with a high level of accuracy.

SUMMARY OF THE INVENTION

It is a primary object of the present invention to provide a method and apparatus for monitoring etching which can monitor the state of etching of a sample to be treated by a dry etching process by clarifying a emission line spectrum.

The monitoring method in accordance with the present invention involves the steps of adjusting a gas pressure in a treating chamber, in which the sample is etched by a dry etching process, to a level such that the emission line spectrum can be clarified, converting the gas whose pressure is thus adjusted to a plasma, and monitoring the state of etching of the sample from the change, with time, of the intensity of the emission line spectrum of the plasma. The monitoring apparatus in accordance with the present invention comprises exhaust means for discharging a gas from a treating chamber in which a sample is treated by a dry etching process, plasma means for introducing the exhaust gas discharged from the treating chamber and converting the gas to a plasma, pressure regulation means for regulating the pressure of the gas of the plasma means to a pressure so that a emission line spectrum is clarified, and spectrum detection means for detecting the bright line spectrum of the plasma in the plasma means and detecting the change, with time, of the intensity of the detected bright line spectrum. Since the emission line spectrum is clarified, the etching state of the sample treated by the dry etching process can be monitored with a high level of accuracy.

DESCRIPTION OF THE PREFERRED EMBODIMENTS

The intensity distribution of an emission spectrum by discharge in a plasma etching apparatus which etches a sample in a dry process changes with a gas pressure in a treating chamber, a discharge system, an applied power, and the like.

On the other hand, silicon (Si) which has been most widely used at present as a material for the substrate of a semiconductor device is etched using a reactive gas containing fluorine, such as $CF_4$ or $SF_6$. In this case, it is believed that Si is etched by the plasma of the reactive gas and it finally turned into $SiF_4$, which is a chemically stable compound. At present, however, a emission line spectrum which is believed to be based upon $SiF_4$ is not found in the emission spectrum. In contrast, the inventor of the present invention has found the emission line spectrum of SiF when Si is etched in a plasma etching apparatus which applies a micro-wave ($\mu$ wave) at a realtively low gas pressure by use of a reactive gas containing F. The inventor has also found from this fact that the emission line spectrum of particles (molecules, atoms, ions) having a relatively small mass number such as SiF by employing a discharge system which keeps a gas pressure at a low level and provides great dissociation.

One embodiment of the present invention will now be described by referring to FIGS. 1 through 4 with reference to a case in which a parallel flat sheet type plasma etching apparatus is used as an etching apparatus.

Figure 1:
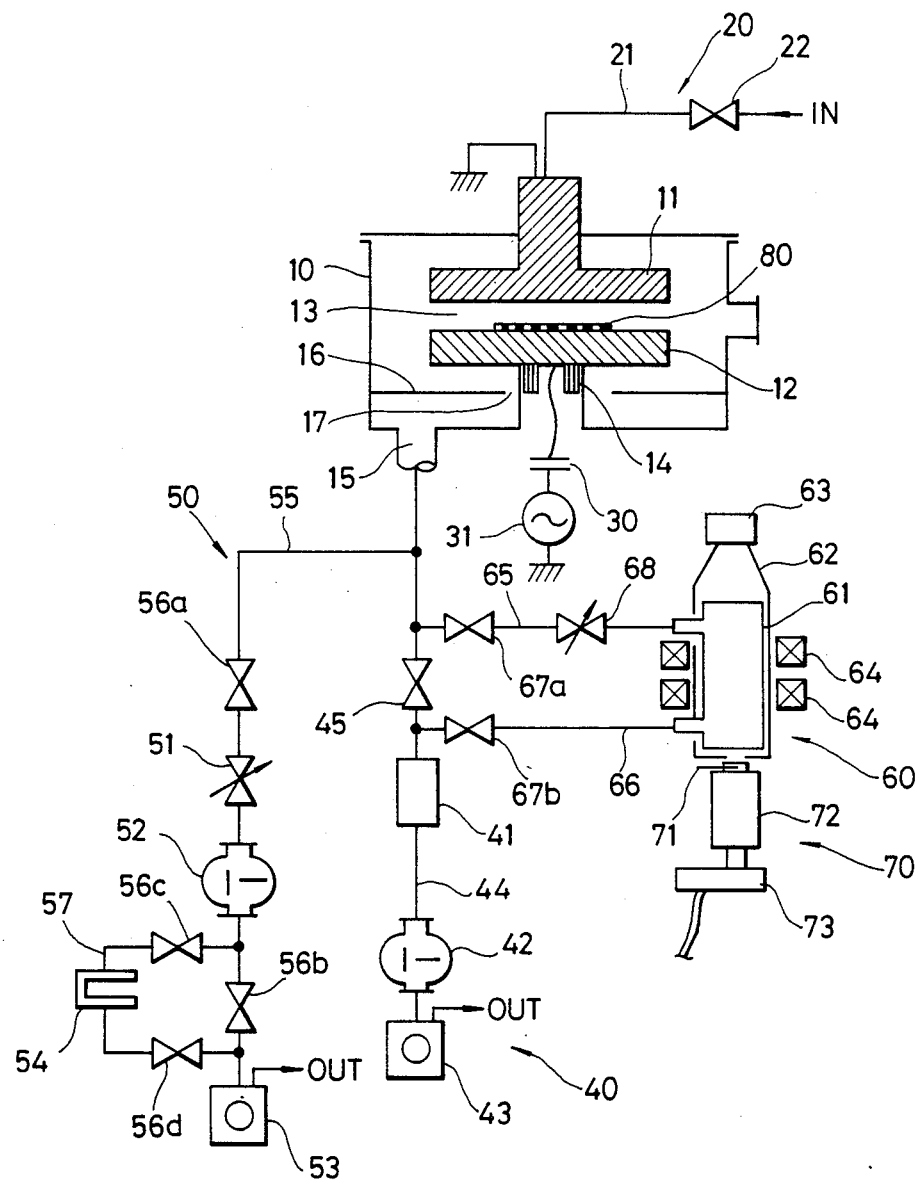
FIG. 1 is a structural block view showing the construction of an etching monitor apparatus in accordance with one embodiment of the present invention.

In FIG. 1, an opposed electrode 11 and a sample electrode 12 are disposed in a treating chamber 10 in parallel with each other in a vertical direction so as to define a discharge space 13 between them. A gas passage (not shown) and a large number of gas emission holes (not shown) are formed on the opposed electrode 11, and each gas emission hole opens to the discharge space 13 and communicates with the gas passage. The opposed electrode 11 is connected to a gas introduction pipe 21 of an etching gas introduction system 20 in communication with the gas passage. A valve 22 is disposed in the gas introduction pipe 21, and its upstream side is connected to an etching gas source (not shown) via a gas flow regulator (not shown). The opposed electrode 11 is grounded.

The sample electrode 12 is electrically isolated from the treating chamber 10 by an insulating material 14, and is connected to a power source such as a radio frequency power source 31 outside the treating chamber 10 via a matching box 30. An exhaust port 15 is defined on the bottom of the treating chamber 10, and a buffle 16 is disposed inside the treating chamber 10 between the reverse of the sample electrode 12 and the bottom of the treating chamber 10. The outer periphery of the buffle 16 extends to each side wall of the treating chamber 10, and a gap 17 is defined between the inner periphery of the buffle 16 and the sample electrode 12.

In FIG. 1, a high vacuum exhaust system 40 consists, for example, of a turbo molecular pump 41, a mechanical booster 42 and a rotary pump 43. The exhaust port 15 of the treating chamber 10 is connected to the suction port of the rotary pump 43 by an exhaust pipe 44. The mechanical booster 42 is disposed upstream of the rotary pump 43 in the exhaust pipe 44, and the turbo molecular pump 41 is disposed further upstream of the booster 42. A valve 45 is disposed in the exhaust pipe 44 upstream of the turbo molecular pump 41.

An etching gas exhaust system 50 consists of a variable orifice 51, the mechanical booster 52, the rotary pump 53 and a trap 54 such as a nitrogen trap (which will be hereinafter called "LN$_2$ trap"). An exhaust pipe 55, which is branched from the portion of the exhaust pipe 44 upstream of the valve 45 is connected to the suction port of the rotary pump 53. The mechanical booster 52 is disposed in this exhaust pipe 55 upstream of the rotary pump 53, and the variable orifice 51, upstream of the mechanical booster 52. A valve 56a is disposed in the exhaust pipe 55 upstream of the variable orifice 51, and a valve 56b between the mechanical booster 52 and the rotary pump 53. The LN$_2$ trap 54 described above is disposed in a by-pass pipe 57 which is branched from the portion of the exhaust pipe 55 between the mechanical booster 52 and the valve 56b and joins again the exhaust upipe 55 between the valve 56b and the rotary pump 53. Valves 56c and 56d are disposed at the inlet and outlet of the LN$_2$ trap 54 in the by-pass pipe 57, respectively.

In FIG. 1, plasma means 60 consists, for example, a sub-chamber 61, a waveguide 62, a magnetron 63 and magnets 64. A gas introduction pipe 65 is branched from the exhaust pipe 44 at the portion between the exhaust pipe 55 and the valve 45, and communicates with a gas introduction port at the upper part of the sub-chamber 61. One of the ends of a gas discharge pipe 66 is connected to a gas discharge port disposed at the lower part of the sub-chamber 61, and the other end is connected to the exhaust pipe 44 at its portion between the valve 45 and the turbo molecular pump 41. A valve 67a is disposed in the gas introduction pipe 65, and pressure regulation means such as a variable orifice 68 is disposed downstream of the valve 67a. A valve 67b is disposed in the gas discharge pipe 66. The sub-chamber 61 is incorporated in the waveguide 62, and the upper end portion of the waveguide 62 is connected to the magnetron 63. The magnets 64 are disposed outside the waveguide 62 in such a manner as to correspond to the positions at which the gas introduction pipe 65 and the gas discharge pipe 66 are connected to the sub-chamber 61, respectively. Spectrum detection means 70 is disposed at the bottom of the sub-chamber 61, that is, at the bottom of the waveguide 62. The spectrum detection means 70 consists, for example, of a slit 71, a spectrometer 72, a photo-multiplier 73, and the like.

A sample 80 is introduced from outside into the treating chamber 10 and is placed on, and held by, the sample electrode 12 with the surface to be etched facing up, as shown in FIG. 1. The valve 45 is them opened and the high vacuum exhaust system 40 is operated to highly evacuate the interior of the treating chamber 10. Next, the treating or etching gas is introduced from the etching gas introduction system 20 into the treating chamber at a predetermined flow rate. While the etching gas exhaust system 50 is being operated to discharge the gas from the treating chamber 10, the radio frequency power source 31 is operated in order to generate the plasma inside the treating chamber 10 and to plasma-etch the surface of the sample 80 to be etched. In this case, part of the gas discharged from the treating chamber 10 is introduced into the sub-chamber 61 through the valve 67a, that is open, and through the variable orifice 68.

The gas pressure in the sub-chamber 61 is regulated and is differentially discharged by the variable orifice 68 to a pressure at which the bright line spectrum can be clarified. Thereafter, the $\mu$ wave is applied by the magnetron 63 and the microwave discharge is generated by the magnets 64 inside the sub-chamber 61. The gas which is introduced into the sub-chamber 61 and whose pressure is regulated is converted afresh to the plasma by the microwave discharge. The spectrum detection means 70 detects the emission line spectrum clarified in the emission spectra, and the etching state of the sample 80, that is, the progress of the etching treatment, is monitored from the change of intensity with time.

EXPERIMENTAL EXAMPLE

Figure 2:
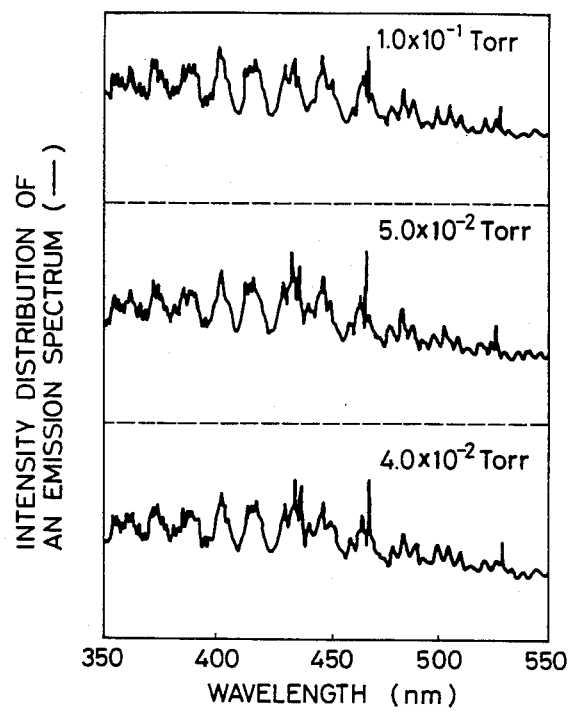
FIGS. 2 and 3 are waveform diagrams showing the relation between the gas pressure in a sub-chamber obtained by the apparatus shown in FIG. 1 and the intensity distribution of an emission spectrum.
Figure 3:
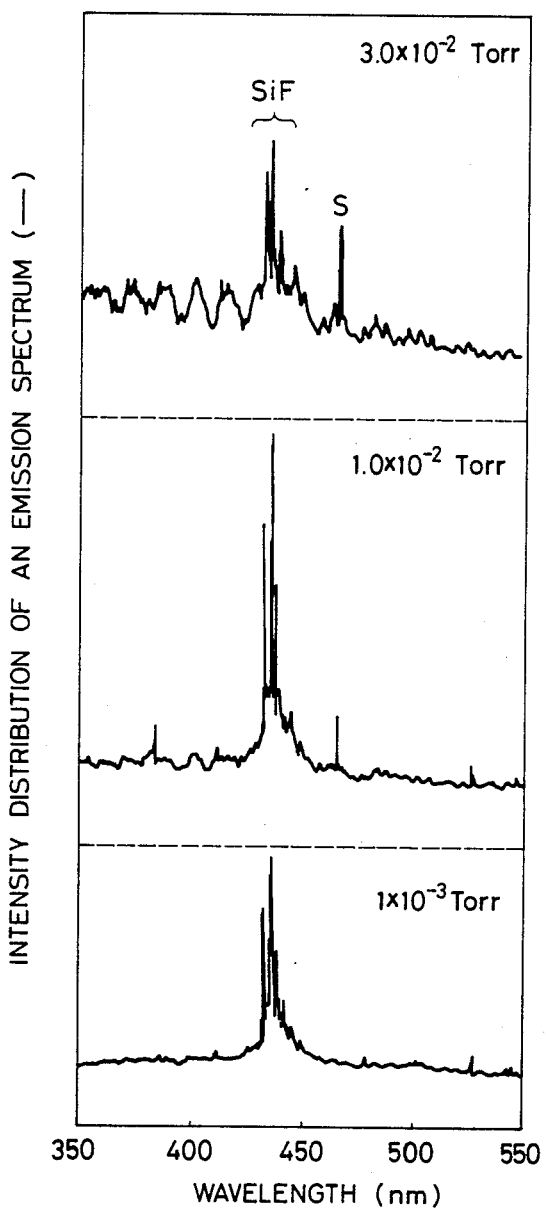

Experiments were carried out using a silicon wafer as the sample 80 and an F-containing reactive gas, i.e., SF$_6$, as the etching gas with the results shown in FIGS. 2 and 3.

FIGS. 2 and 3 show the relation between the gas pressure inside the sub-chamber 61 and the intensity distribution of the emission spectra. When the gas pressure inside the sub-chamber 61 was regulated below $4.0 \times 10^{-2}$ Torr, the emission line spectrum of SiF containing Si, that was otherwise ambiguous at a lower gas pressure, became distinct. Among these spectra, one having the maximum peak was a emission line spectrum of a 440 nm wavelength. In this case, the gas pressure of SF$_6$ inside the treating chamber 10 was kept constant at 0.15 Torr.

Figure 4:
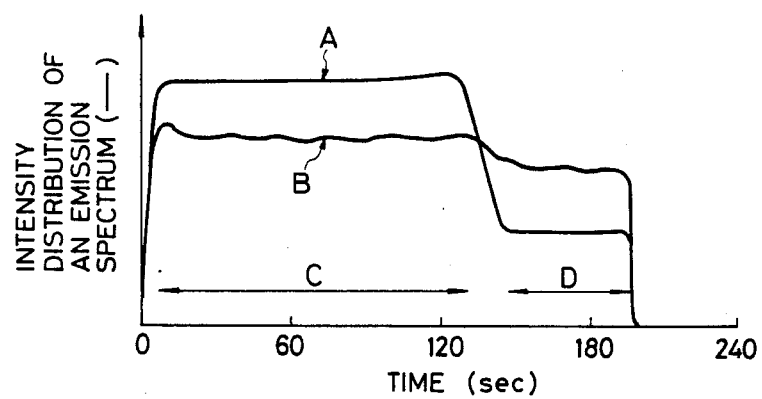
FIG. 4 is a diagram showing comparatively the change, with time, of the intensity of a emission line spectrum of a 440 nm wavelength and the change, with time, of the intensity of an emission spectrum of a 440 nm wavelength in a treating chamber.

FIG. 4 shows comparatively the change, with time, of the intensity of a emission line spectrum of 440 nm wavelength in the sub-chamber (Curve A) with the change, with time, of intensity of an emission spectrum of a 440 nm wavelength in the treating chamber (Curve B) When polycrystalline Silicon (Poly-Si; primer material=SiO$^2$) is etched in the treating chamber. In this case, the gas pressure of SF$_6$ in the treating chamber 10 was 0.15 Torr, the gas pressure in the sub-chamber 61 was $1.0 \times 10^{-2}$ Torr, and the flow rate of SF$_6$ was 100 cc/min. As can be understood from FIG. 4, when monitor was made using the emission line spectrum of the 440 nm wavelength, the changes of intensity of spectra were extremely great during the etching of poly-Si Peoriod C and the etching of SiO$_2$ Peoriod D as the primer material, the etching state could be monitored with a high level of accuracy, and the end of etching could be detected also with a high level of accuracy.

Experiments were also carried out in the same way as above using tungsten, molybdenum, $SiO_2$, $Si_3N_4$, tungsten silicide and molybdenum silicide. It was found out from the experiments that when the gas pressure was below $4.0 \times 10^{-2}$ Torr inside the sub-chamber 61, the emission line spectra of the respective materials appeared distinctively irrespective of the materials.

The embodiment described above provides the following effects.

(1) The emission line spectrum can be clarified. The etching state of the sample in the treating chamber can be monitored with a high level of accuracy by detecting the change of the intensity of the emission line spectrum with time.

(2) Since the etching state of the sample in the treating chamber can be monitored highly accurately, any variance of etching between a plurality of samples can be reduced, and hence the etching yield can be improved.

Figure 5:
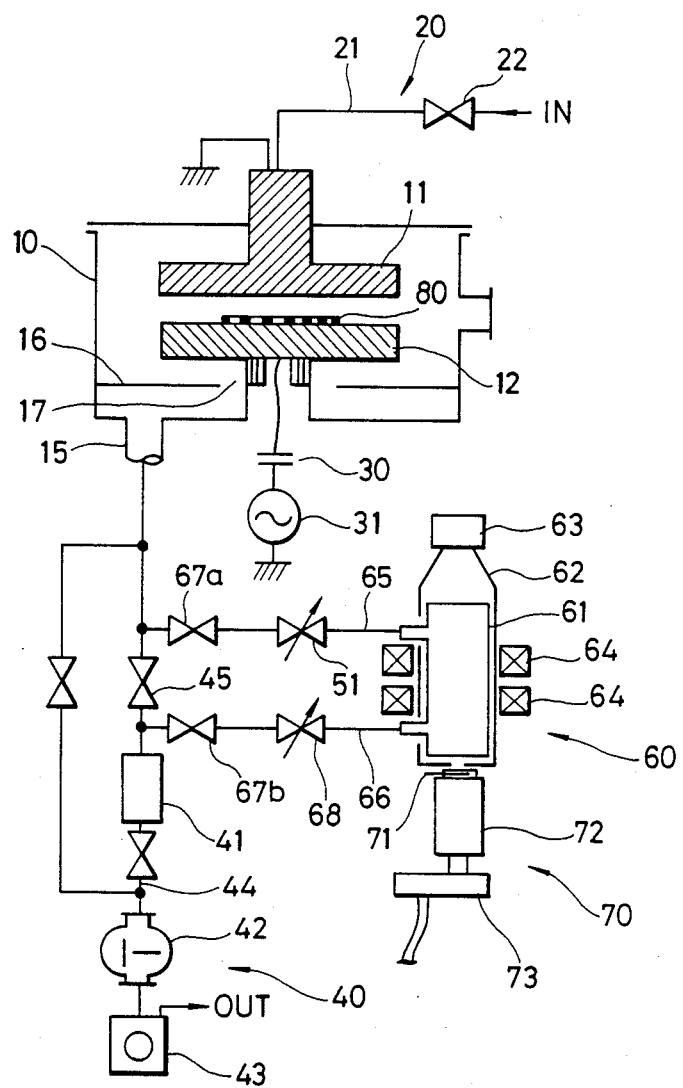
FIG. 5 is a structural block view showing an etching monitor apparatus in accordance with a second embodiment of the present invention.

FIG. 5 shows another embodiment of the present invention. Unlike the first embodiment, this embodiment exhausts the whole of the gas discharged from the treating chamber 10 during etching of the sample 80 by the high vacuum exhaust system 40 through the sub-chamber 61. The variable orifice 51 in FIG. 1 of the first embodiment is disposed in the gas introduction pipe 65 downstream of the valve 67a in this embodiment, and the variable orifice 68 as the pressure regulation means is disposed in the gas discharge pipe 66 upstream of the valve 67b. The other constituents in this embodiment are represented by similar reference numerals as in FIG. 1 and the explanation of such constituents is omitted.

This embodiment provides the same action and effect as the first embodiment. Since this embodiment can eliminate the treating gas exhaust system used in the first embodiment, the exhaust system can be simplified and the cost of production of the apparatus can be reduced.

Figure 6:
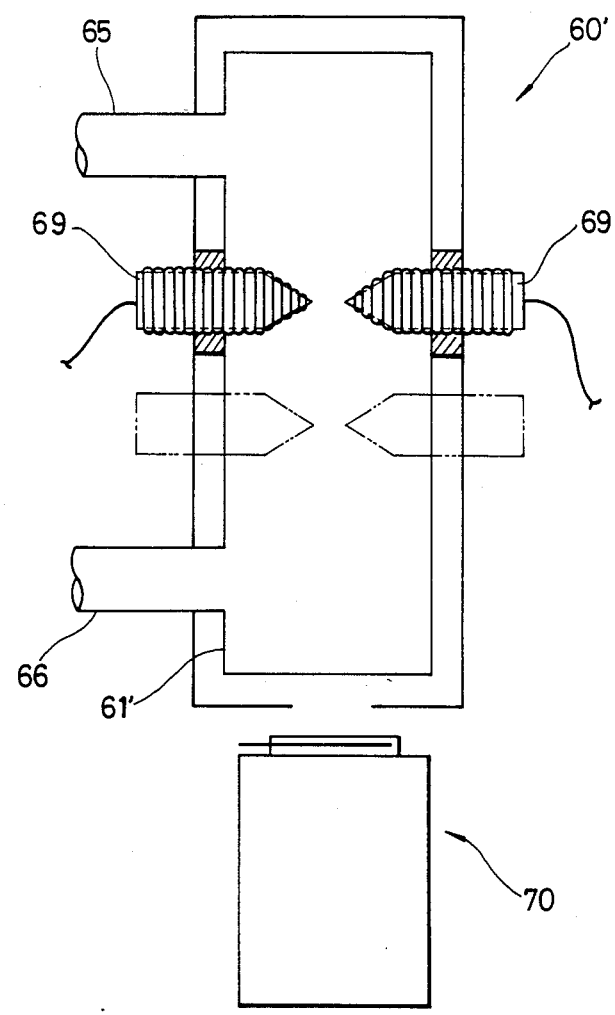
FIG. 6 is a structural block view of plasma means of the etching monitor apparatus in accordance with a third embodiment of the present invention.

FIG. 6 shows a third embodiment of the present invention. The plasma means 60' in this embodiment consists of the sub-chamber 61' equipped with the gas introduction pipe 65 at is upper portion and with the gas discharge pipe 66 at its lower portion, and projection members 69 connected to a power source (not shown). The projection members 69 are disposed at the intermediate portion of the sub-chamber 61' in such a fashion that their ends, not connected to the power source, face each other inside the sub-chamber 61'. The emission spectrum detection means 70 is disposed in such a fashion as to correspond to the bottom of the sub-chamber 61'. The projection members 69 are made of a material different from the sample.

During the etching of the sample (not shown), part of the gas discharged from the treating chamber (not shown) is introduced into the sub-chamber 61' through the valve disposed in the gas introduction pipe 65 (not shown) and through the variable orifice (not shown). The gas pressure inside the sub-chamber 61' is regulated in the same way as in the foregoing embodiments. When a high voltage is applied from the power source to the projection members 69, spark discharge is generated between these members. The gas which is introduced into the sub-chamber 61' and whose pressure is regulated is afresh converted to the plasma by this spark discharge. The spectrum detection means 70 detects the clarified emission line spectrum in the emission spectra of this plasma, and the progress of the etching process of the sample can be detected highly accurately from the change of the intensity with time.

This embodiment provides the same effect as the first embodiment, and since the plasma means can be simplified, the cost of production of the apparatus can be further reduced.

Although the foregoing embodiments etch the sample by the dry etching process using the plasma, etching treatment of the sample by the dry etching process without using the plasma, such as etching treatment which excites a reactive gas by light and etches the sample, may also be employed.

As described above, the method of monitoring etching in accordance with the present invention comprises the steps of regulating the gas pressure inside the treating chamber in which the sample is etched by the dry etching process to a pressure at which the emission line spectrum can be clarified, converting the gas whose pressure is thus regulated to the plasma, and monitoring the etching state of the sample from the change, with time, of the intensity of the emission line spectrum of the plasma. The apparatus for monitoring etching in accordance with the present invention comprises exhaust means for discharging the gas from the treating chamber in which the sample is etched by the dry etching process, the plasma means for introducing the gas discharged from the treating chamber and converting the gas to the plasma, the pressure regulation means for regulating the pressure of the gas to a pressure at which the emission line spectrum can be clarified, and the spectrum detection means for detecting the emission line spectrum of the plasma of the plasma means, and detecting the change, with time, of the intensity of the detected emission line spectrum. Therefore, the present invention provides the effect that the emission line spectrum can be clarified, and the etching state of the sample which is being etched by the dry etching process can be monitored highly accurately.

What is claimed is:

1. A method of monitoring etching which comprises the steps of:
    regulating a gas pressure in a treating chamber, in which a sample is being etched by a dry etching process, to a pressure at which a emission line spectrum can be clarified;
    Converting the gas having the pressure thereof regulated to plasma; and
    monitoring the etching state of said sample from the change of the intensity of the emission line spectrum of the plasma with time.

2. The method of monitoring etching as defined in claim 1 wherein the gas having the pressure thereof regulated is converted to the plasma by discharge having great dissociation.

3. The method of monitoring etching as defined in claim 2 wherein the gas having the pressure thereof regulated is converted to the plasma by microwave discharge.

4. The method of monitoring etching as defined in claim 2 wherein the gas having the pressure thereof regulated is converted to the plasma by spark discharge.

5. The method of monitoring etching as defined in claim 1 wherein the pressure of the gas to be converted to the plasma is regulated to a pressure of up to $4.0 \times 10^{-2}$ Torr.

6. The method of monitoring etching as defined in claim 5 wherein said sample is a sample having a polycrystalline silicon film, and said emission line spectrum is that of silicon fluoride.

7. The method of monitoring etching as defined in claim 6 wherein said emission line spectrum of silicon fluoride is a emission line spectrum having a 440 nm wavelength, and the etching state of said sample is monitored from the change of the intensity of said emission line spectrum with time.

8. An apparatus for monitoring etching which comprises:
   exhaust means for discharging a gas from a treating chamber in which a sample is being etched by a dry etching process;
   plasma means for introducing said gas discharged from said treating chamber and converting it to plasma;
   pressure regulation means for regulating the pressure of said gas at said plasma means to a pressure at which a emission line spectrum can be clarified; and
   spectrum detection means for detecting the emission line spectrum of said plasma at said plasma means, and detecting the change of the intensity of said detected emission line spectrum with time.

9. The apparatus for monitoring etching as defined in claim 8 wherein said plasma means consists of a sub-chamber into which said gas discharged from said treating chamber is introduced, a waveguide incorporating therein said sub-chamber and connected to a magnetron, and magnets generating microwave discharge together with said magnetron inside said sub-chamber.

10. The apparatus for monitoring etching as defined in claim 8 wherein said plasma means consists of a sub-chamber into which said gas discharged from said treating chamber is introduced, and projection members, each having one of the ends thereof connected to a power source and the other end disposed in such a manner as to face the other end of the other of said projection members inside said treating chamber.

11. The apparatus for monitoring etching as defined in claim 10 wherein said projection members are made of a material different from that of said sample.

* * * * *